(12) United States Patent
Simon Ludovic et al.

(10) Patent No.: US 11,311,472 B2
(45) Date of Patent: Apr. 26, 2022

(54) TOPICAL COMPOSITION COMPRISING CROSSLINKED HYALURONIC ACID AND A POLYACRYLATE COMPOUND

(71) Applicant: TEOXANE, Geneva (CH)

(72) Inventors: Jean-marie Simon Ludovic, Vouvry (CH); Nicolas Mackiewicz, Denges (CH)

(73) Assignee: TEOXANE, Geneva (CH)

( * ) Notice: Subject to any disclaimer, the term of this patent is extended or adjusted under 35 U.S.C. 154(b) by 37 days.

(21) Appl. No.: 16/647,159

(22) PCT Filed: Sep. 18, 2017

(86) PCT No.: PCT/IB2017/001302
§ 371 (c)(1),
(2) Date: Mar. 13, 2020

(87) PCT Pub. No.: WO2019/053486
PCT Pub. Date: Mar. 21, 2019

(65) Prior Publication Data
US 2021/0244644 A1    Aug. 12, 2021

(51) Int. Cl.
*A61K 8/81*   (2006.01)
*A61K 8/04*   (2006.01)
(Continued)

(52) U.S. Cl.
CPC ........... *A61K 8/8147* (2013.01); *A61K 8/042* (2013.01); *A61K 8/731* (2013.01); *A61K 8/735* (2013.01); *A61Q 19/08* (2013.01); *A61K 2800/30* (2013.01); *A61K 2800/594* (2013.01); *A61K 2800/87* (2013.01)

(58) Field of Classification Search
None
See application file for complete search history.

(56) References Cited

U.S. PATENT DOCUMENTS 9,408,797 B2 *   8/2016   Njikang ................. A61K 8/735

FOREIGN PATENT DOCUMENTS

| EP | 3120831 A1 | 1/2017 |
| FR | 3041251 A1 | 3/2017 |
| WO | 2017/009206 A1 | 1/2017 |

OTHER PUBLICATIONS

International Search Report for PCT/IB2017/001302 dated Feb. 12, 2018 (4 pages).

(Continued)

*Primary Examiner* — Kyung S Chang
(74) *Attorney, Agent, or Firm* — Shumaker, Loop & Kendrick, LLP

(57) ABSTRACT

Disclosed is a sterile and topical cosmetic composition including, in a physiologically acceptable medium, an efficient amount of crosslinked hyaluronic acid and an efficient amount of polyacrylate crosspolymer-6, Also disclosed is the use of said composition for reducing the signs of skin aging and/or to car the skin of a subject who has previously been subjected to one or more aesthetic and/or cosmetic intervention(s); and to a cosmetic process for caring the skin comprising at least the step of applying topically, on the skin surface(s) to be cared, an effective amount of said composition, to a subject who has previously been subjected to one or more aesthetic and/or cosmetic intervention(s).

14 Claims, 1 Drawing Sheet

(51) Int. Cl.
A61K 8/73 (2006.01)
A61Q 19/08 (2006.01)

(56) References Cited

OTHER PUBLICATIONS

Written Opinion for PCT/IB2017/001302 dated Feb. 13, 2018 (6 pages).
Annonymous: "GNPD—Multi-Molecular Hyaluronic Complex", Jul. 1, 2015 XP055444284 (4 pages; retrieved Jan. 25, 2018).
Anonymous: "GNPD—Anti-Ageing Lotion SPF 15", Apr. 1, 2015, XP055444703, (4 pages, retrieved Jan. 25, 2018).
Anonymous; "GNPD—Back Into the Roots 10-minute Stimulating Scalp Masque", Aug. 1, 2016, XP055444310 (2 pages, retrieved Jan. 25, 2018).
Evonik: Instantly Fills Lines & Wrinkles, Apr. 1, 2008, XP055444318 (8 pages, retrieved Jan. 25, 2018).

* cited by examiner

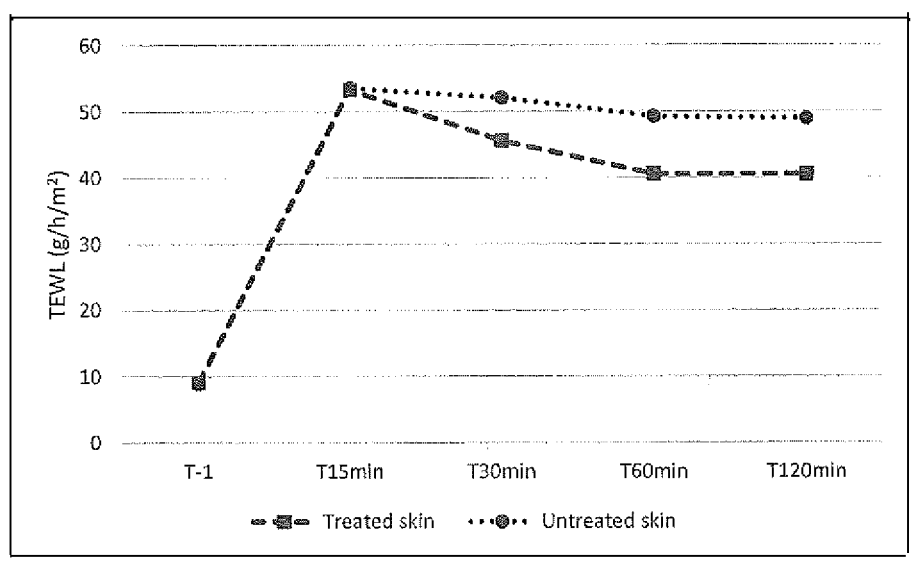

TOPICAL COMPOSITION COMPRISING CROSSLINKED HYALURONIC ACID AND A POLYACRYLATE COMPOUND

TECHNICAL FIELD AND BACKGROUND

The present invention relates to a sterile cosmetic crosslinked hyaluronic acid based-composition for topical application, useful for reducing signs of aging in a subject previously been subjected to one or more aesthetic and/or cosmetic intervention(s).

In the aesthetic field, there have been efforts to develop anti-aging compositions useful to correct skin defects such as scars and wrinkles in a subject, and to augment soft tissue volume, to improve skin appearance, particularly facial skin appearance.

The principal aesthetic intervention employed to correct such defects involves injecting a filler composition into the dermal layer of the skin where the tissue augmentation and/or the correcting effect is desired. Other aesthetic and/or cosmetic interventions purportedly achieve a similar purpose such as botulinum toxin injection, peeling (e.g. chemical peeling), micro-needling, mesotherapy, lipo-filling, injection of platelet-rich human plasma, radiofrequency, dermabrasion and lasers use.

Injectable soft tissue filler compositions, such as dermal filler(s), can comprise biodegradable and biocompatible materials such as collagen, hyaluronic acid, calcium hydroxylapatite, poly-L-lactic acid (PLLA) and mixtures thereof. Due to in vivo metabolization of said compositions, repeated injections are needed over time to maintain the desired aesthetic effects.

For over fifteen years, hyaluronic acid compositions have been widely used in the aesthetic and cosmetic fields and have proved to be harmless and effective.

However, most of the currently used aesthetic and/or cosmetic interventions may have unwanted side-effects. These side effects may include, but are not limited to, edemas, bruising, bleeding, discomfort, infection, persistent or temporary swelling, redness, itching, erythema, sensitivity, localized pallor, irregularities, small hematoma, acute or chronic inflammatory reactions, abscesses, headache, paraesthesia, nausea, facial pain and granulomatous reactions. These reactions are located at and/or near the skin surface(s) of the subject.

Further, one drawback of the currently used aesthetic and/or cosmetic interventions is that they are traumatic for the skin's barrier, i.e. they may involve a weakening of the skin's barrier which means a risk of skin dehydration and/or transient damage(s) of skin quality. These effects may be due to skin damage/trauma during the aesthetic and/or cosmetic intervention often associated with the use of needles.

Another drawback of injection procedures is that subjects often experience painful sensation(s), which can be further exacerbated with increased viscosity and/or elasticity of the administered composition.

SUMMARY

Accordingly, there is a need for a cosmetic composition that avoids the above-mentioned drawbacks and side-effects. There remains also a need to provide cosmetic compositions that improve skin quality and restore the skin barrier's integrity after one or more aesthetic and/or cosmetic intervention(s) such as those mentioned above.

There remains also a need to provide cosmetic compositions that reduce a subject's unpleasant experience and/or unwanted side effects, e.g. weakening of the skin's barrier, after one or more aesthetic and/or cosmetic traumatic intervention(s) thus, advantageously mitigating the subject's reluctance to repeat such interventions.

There also remains a need to provide cosmetic compositions whose anti-aging effect(s) diminishes the frequency of traumatic aesthetic and/or cosmetic interventions such as those mentioned above.

There also remains a need to provide cosmetic compositions that enhance skin healing at, and/or near to, the skin surface(s) cared with one or more traumatic aesthetic and/or cosmetic intervention(s) such as those mentioned above.

Against all expectations, the inventors have discovered that the combination of an efficient amount of crosslinked hyaluronic acid with an efficient amount of a specific anionic associative polymer in a sterile and topical cosmetic composition allows satisfies the above-mentioned, long-felt needs.

Until now, although topical anti-aging compositions comprising un-crosslinked, slightly crosslinked or even low amount(s) of crosslinked hyaluronic acid have already been proposed, no document describes a topical anti-aging composition implementing a high amount of crosslinked hyaluronic acid gel.

Indeed, implementation of crosslinked hyaluronic acid in topical composition implies difficulties in terms of stability, homogeneity (due to problems such as sedimentation and de-polymerization) and/or texture modification, especially when the composition has to be heat sterilized.

Moreover, it is known that in the presence of a high amount of additional compounds such as minerals, formulations lose their stability as they are generally not resistant to electrolytes.

Thus, it remained a need in the art to provide a cosmetic composition comprising a crosslinked hyaluronic acid gel that is stable when subjected to high temperatures and pressures (for example under heat sterilization such as autoclaving) and/or when stored at ambient temperature for an extended period of time, which does not sediment, which presents a smooth non fluffy texture and which overcomes above-mentioned drawbacks.

Thus, according to a first aspect, disclosed is a sterile and topical cosmetic composition comprising, in a physiologically acceptable medium, an efficient amount of crosslinked hyaluronic acid and an efficient amount of polyacrylate crosspolymer-6.

The present disclosure further discloses a sterile and topical cosmetic composition comprising, in a physiologically acceptable medium, at least one crosslinked hyaluronic acid and at least one polyacrylate crosspolymer-6.

According to another aspect, also disclosed is the use of a sterile and topical cosmetic composition comprising in a physiologically acceptable medium, an efficient amount of crosslinked hyaluronic acid and an efficient amount of polyacrylate crosspolymer-6 for reducing the signs of skin aging and/or to care the skin of a subject who has previously been subjected to one or more aesthetic and/or cosmetic intervention(s) such as injection of a dermal filler composition, injection of botulinum toxin, peeling (e.g. chemical peeling), micro-needling, mesotherapy, lipo-filling, injection of platelet-rich human plasma, radiofrequency, dermabrasion and lasers use, preferably to one or more micro-needling procedure(s).

Thus, according to a preferred embodiment, the subject was previously subjected to one or more micro-needling procedure(s).

According to another aspect, also disclosed is a cosmetic process for caring the skin comprising at least the step of applying topically, on the skin surface(s) to be cared, an effective amount of a sterile and topical cosmetic composition in accordance with the invention, to a subject who has previously been subjected to one or more aesthetic and/or cosmetic intervention(s) such as injection of a dermal filler composition, injection of botulinum toxin, peeling (e.g. chemical peeling), micro-needling, mesotherapy, lipo-filling, injection of platelet-rich human plasma, radiofrequency, dermabrasion and lasers use, preferably to one or more micro-needling procedure(s).

Also provided herein is a cosmetic method for reducing the skin aging comprising the steps of topically apply on the skin surface(s) to be cared, an effective amount of a sterile and topical cosmetic composition in accordance with the invention, to a subject who has previously been subjected to one or more aesthetic and/or cosmetic intervention(s) such as injection of a dermal filler composition, injection of botulinum toxin, peeling (e.g. chemical peeling), micro-needling, mesotherapy, lipo-filling, injection of platelet-rich human plasma, radiofrequency, dermabrasion and lasers use, preferably to one or more micro-needling procedure(s).

BRIEF DESCRIPTION OF THE DRAWINGS

These and other features, aspects and advantages of the present invention are better understood when the following detailed description of the invention is read with reference to the accompanying drawings, in which: FIG. 1 depicts Trans-Epidermal Water Loss (TEWL) over time, and more particularly at T-1, T15 min, T30 min, T60 min and T120 min both for untreated skin and for skin treated by a composition in accordance with the invention (e.g., composition 1 of Example 1).

DETAILED DESCRIPTION

Definitions

For the purpose of the present invention, the term "sterile", relates to an environment ensuring the safety required for preparing a composition which can be safely used by topical administration on damaged skin surfaces and/or relates to a composition which is prepared in a sterile environment or made sterile with a sterilization method which may be chosen among the ones known by the one skilled in the art. Indeed, for obvious reasons, it is essential that a composition in accordance with the invention be devoid of any contaminant capable of initiating an undesirable side reaction at the host organism.

the term "topical" refers to a composition which is intended to be applied on the skin surface of a subject.

the expression "on the skin surface" includes the epidermis of a subject, such as its facial epidermidis.

the term "effective amount" in the expression "effective amount of a cosmetic composition" relates to the amount of said cosmetic composition which needs to be applied on the skin surface to be cared in order to produce an anti-aging and/or a caring effect.

the term "hyaluronic acid" includes hyaluronic acid, its salts such as physiologically acceptable salts such as the sodium salt, the potassium salt, the zinc salt and the silver salt, its derivatives and mixture thereof.

the term "molecular weight" of hyaluronic acid is to be understood as indicating the weight average molecular weight (Mw) in Daltons (Da). Said molecular weight is calculated from an intrinsic viscosity measurement using the following Mark-Houwink relation:

Intrinsic Viscosity $(m^3/kg) = 9.78 \times 10^5 \times Mw^{0.690}$.

the term "crosslinked hyaluronic acid" means a water insoluble hyaluronic acid formed by reacting an un-crosslinked hyaluronic acid, one of its salts, one of its derivatives or a mixture thereof, with a crosslinking agent under suitable reaction conditions. Said crosslinked hyaluronic acid may be in form of a powder, a gel, a liquid and/or a solid and dense three dimensional network as obtained just after crosslinking and before any swelling step and may include mixtures of crosslinked hyaluronic acids, mixtures of salts of crosslinked hyaluronic acids, mixture of crosslinked hyaluronic acid derivatives or mixtures of at least one crosslinked hyaluronic acid and/or at least one salt of crosslinked hyaluronic acid and/or at least one crosslinked hyaluronic acid derivatives.

For purpose of this invention, the term "efficient amount" in the expression "efficient amount of crosslinked hyaluronic acid" relates to the amount of crosslinked hyaluronic acid which is needed to have a composition with filmogenic properties, i.e. film-forming effect which allows to limit the dehydration of the skin and/or the progressive release of additional compounds, such as antioxidants and minerals, which may be incorporated in the composition.

the term "crosslinking agent" relates to any compound capable of inducing a crosslinking between the chains of hyaluronic acid.

the term "anionic associative polymer" refers to a compound with a hydrophobic part and a hydrophilic part, its hydrophilic part being negatively charged. Said anionic associative polymer may be use as a thickener agent and/or as a surfactant in cosmetic compositions.

the term "polyacrylate crosspolymer-6" includes polyacrylate crosspolymer-6, derivatives of polyacrylate crosspolymer-6 and mixture thereof.

the term "efficient amount" in the expression "efficient amount of polyacrylate crosspolymer-6" relates to the amount of polyacrylate crosspolymer-6 which is needed to have a stable composition with a smooth and a non-granular aspect.

the term "stable" relates to a composition which keeps its homogeneity and/or which does not demonstrate any significant change in its mechanical and/or organoleptic properties over time (e.g., for at least 3 months, for at least 6 months, for at least 9 months).

the term "on the skin surface to be cared" refers to a skin surface onto which and/or close to which one or more aesthetic and/or cosmetic intervention(s) has(have) previously been carried out. The term "close to" meaning a circular area around the skin surface to be cared with an average diameter of 10 cm, more preferably 5 cm.

the expression "aesthetic and/or cosmetic intervention" refers to an act useful to correct defects in skin such as scars, wrinkles and/or others signs of aging and/or to augment the soft tissue volume of a subject in order to improve the appearance of his skin. Among aesthetic and/or cosmetic interventions in accordance with the invention it may be cited: injection of a dermal filler composition, injection of botulinum toxin, peeling (e.g. chemical peeling), micro-needling, mesotherapy, lipo-filling, injection of platelet-rich human plasma, radiofrequency, dermabrasion and lasers use.

the term "dermal filler composition" relates to an injectable composition comprising biodegradable and biocompatible materials such as crosslinked and/or non-crosslinked collagen, crosslinked and/or non-crosslinked hyaluronic acid, calcium hydroxylapatite or poly-L-lactic acid (PLLA).

the term "injection of botulinum toxin" refers to the procedure comprising a step of injecting a composition comprising an adequate amount of botulinum toxin, one of its derivatives and/or a mixture thereof, for causing a muscle relaxation resulting in the smoothing of the overlying skin thus reduction of wrinkles.

the term "peeling" means removing a controlled amount of the skin's outer layers to promote its regeneration and repair, thus improving its health and appearance. For example, a chemical peeling involves the use of chemical substances for said removing of outer layers of the skin.

the term "micro-needling" relates to the puncture of the skin to various depths with very fine needles. This procedure causes a controlled injury inducing the skin to synthetize more collagen thus having an anti-aging effect and improving the skin aspect of the subject.

the term "mesotherapy" relates to a procedure comprising multiple injections into the skin of a mixture of one or more ingredients, such as minerals and vitamins.

the term "lipo-filling" refers to a plastic surgery procedure in which tissue defects are filled with autografted fat tissue.

the term "injection of platelet-rich human plasma" relates to a procedure comprising the step of injecting through the skin of a subject its own enriched autologous plasma notably in order to rejuvenate and/or slow down the aging process of his skin, in particular the skin of its face.

the term "radiofrequency" refers to the heating of tissues and stimulation of subdermal collagen synthesis with radiofrequency energy in order to reduce the appearance of fine lines and/or loose skin. This technique induces tissue remodeling and synthesis of new collagen and elastin.

the term "dermabrasion" relates to a technique comprising a step of removing superficial skin layers with a rapidly revolving abrasive tool.

the term "lasers" relates to the use the laser technology for conducting different kinds of aesthetic and/or cosmetic treatments, such as epilation, wrinkles attenuation and naevus (birthmark) elimination.

the term "previously" in the expression "a subject who has previously been subjected to one or more aesthetic and/or cosmetic intervention(s)" means that at least one intervention has been carried out within the hour before and up to one month before administration of a composition in accordance with the invention, preferably within the hour before said administration.

A "physiologically acceptable medium" means a medium devoid of toxicity and compatible with the application of a composition such as considered in the present invention.

Crosslinked Hyaluronic Acid

As above-mentioned, the present invention discloses a crosslinked hyaluronic acid into a topical cosmetic composition.

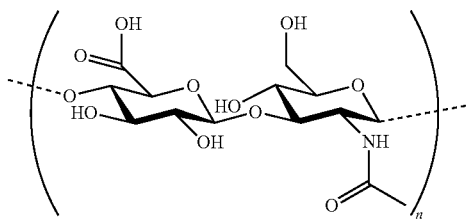

Hyaluronic acid, also called hyaluronan or hyaluronate, is a linear non-sulfated glycosaminoglycan composed of repeating units of D-glucuronic acid and N-acetyl-D-glucosamine (Tammi R, Agren U M, Tuhkanen A L., Tammi M. *Hyaluronan metabolism in skin. Progress in Histochemistry & Cytochemistry* 29 (2): 1.-81, 1994).

The term "at least one crosslinked hyaluronic acid" includes mixtures of crosslinked hyaluronic acids, mixtures of salts of crosslinked hyaluronic acids or mixtures of crosslinked hyaluronic acids and salts of crosslinked hyaluronic acids. The hyaluronic acid used for preparing a crosslinked hyaluronic acid in accordance with the invention may be more preferably chosen from hyaluronic acid physiologically acceptable salts such as the sodium salt, the potassium salt, the zinc salt, the silver salt and mixtures thereof.

One particularly preferred salt of hyaluronic acid is sodium hyaluronate (NaHA).

Preferably, the hyaluronic acid used for preparing a crosslinked hyaluronic acid in accordance with the invention has a high average molecular weight, preferably ranging from about 50 000 to about 10 000 000 Daltons, preferably from about 500 000 to about 4 000 000 Daltons, more preferably from about 1 000 000 to about 2 000 000 Daltons.

As above-mentioned, crosslinked hyaluronic acid is applied topically in an efficient amount so as to obtain the desired effect(s).

A crosslinked hyaluronic acid suitable for the present invention can be obtained by any conventional technique of crosslinking with at least one crosslinking agent. In particular, it may be referred to the U.S. Pat. No. 9,353,194. Preferably, the crosslinked hyaluronic acid is obtained by crosslinking at least one non-crosslinked hyaluronic acid with at least one crosslinking agent.

The choice of this crosslinking agent clearly falls within the competence of a person skilled in the art.

A crosslinking agent in accordance with the invention is preferably a multifunctional crosslinking agent, more preferably a crosslinking agent with two reactive functions.

A crosslinking agent in accordance with the invention may be an epoxy crosslinking agent or a non-epoxy crosslinking agent.

As a non-epoxy crosslinking agent, it can be cited for example: endogenous polyamines, aldehyde, carbodiimide and divinylsulfone.

Preferably, a crosslinking agent in accordance with the invention is an epoxy crosslinking agent.

An epoxy crosslinking agent in accordance with the present invention may preferably be selected from the group consisting of 1,4-butanediol diglycidyl ether (BDDE), 1,2,7,8-diepoxyoctane (DEO), 1,2-bis(2,3-epoxypropyl)-2,3-ethylene, 1,4-bis(2,3-epoxypropoxy)butane, 1,4-bisglycidyloxybutane, 1,2-bis(2,3-epoxypropoxy)ethylene, and 1-(2,3-epoxypropyl)-2,3-epoxycyclohexane, and mixtures thereof.

Preferably, a crosslinking agent in accordance with the invention is 1,4-butanediol diglycidyl ether (BDDE).

The crosslinked hyaluronic acid, has preferably a degree of crosslinking ranging from about 0.1 to about 20%, preferably from about 3 to about 12%, more preferably from about 8 to about 11%.

For purpose of the present invention, the term "degree of crosslinking" is defined by the percentage of the weight ratio between the mass of crosslinking agent relative to the mass of hyaluronic acid which are used for the crosslinking, i.e. m(BDDE)/m(hyaluronic acid to be crosslinked) multiplied by 100.

Preferably, the crosslinked hyaluronic acid comprised in a composition in accordance with the invention is in a gel form.

A crosslinked hyaluronic acid gel in accordance with the invention may comprise from about 10 mg/g to about 35 mg/g, preferably from about 15 mg/g to about 30 mg/g, still more preferably from about 20 mg/g to about 25 mg/g of total hyaluronic acid with respect to the total weight of the crosslinked hyaluronic acid gel.

A crosslinked hyaluronic acid gel in accordance with the invention may comprise a mixture of crosslinked and un-crosslinked hyaluronic acid where the amount of crosslinked hyaluronic acid is comprised between about 50% by weight and about 99% by weight preferably between about 60% by weight and about 90% by weight, still more preferably between about 70% by weight and about 90% by weight with respect to the total weight of crosslinked hyaluronic acid gel and the amount of un-crosslinked hyaluronic acid is comprises between about 1% by weight and about 50% by weight preferably between about 10% a by weight nd about 40% by weight, still more preferably between about 10% by weight and about 30% by weight, with respect to the total weight of crosslinked hyaluronic acid gel.

A crosslinked hyaluronic acid gel in accordance with the present invention may be present in a composition in accordance with the invention in a large amount, i.e. in an amount ranging from about 5% to about 99.5% by weight, preferably ranging from about 7% to about 50% by weight, more preferably from about 9% to about 20% by weight, still more preferably from about 10% to about 15% by weight, with respect to the total weight of the composition.

A crosslinked hyaluronic acid in accordance with the present invention may be present in a composition in accordance with the invention in an amount ranging from about 0.10% to about 0.60% by weight, preferably from about 0.20% to about 0.50% by weight, more preferably from about 0.25% to about 0.30% by weight, still more preferably from about 0.28% to about 0.29% by weight, with respect to the total weight of the composition.

As shown in the examples, the use of crosslinked hyaluronic acid versus un-crosslinked hyaluronic acid in a composition in accordance with the invention has a beneficial impact in terms of stability, in particular homogeneity and texture.

The use of an efficient amount of crosslinked hyaluronic acid in a composition in accordance with the present invention is advantageous as it provides, as shown in the examples, a film-forming effect which allows to limit the dehydration of the skin and/or the progressive release of additional compounds such as antioxidants and minerals which may be incorporated in the composition.

Polyacrylate Crosspolymer-6

In addition to including a physiologically medium and an efficient amount of crosslinked hyaluronic acid as disclosed above, the composition comprises an efficient amount of polyacrylate crosspolymer-6.

Polyacrylate crosspolymer-6 (INCI name) is an associative anionic polymer and more particularly is a copolymer of ammonium acryloyldimethyltaurate, dimethylacrylamide, lauryl methacrylate and laureth-4 methacrylate crosslinked with trimethylolpropane triacrylate, still more particularly an anionic terpolymer of 2-methyl-2-[(1-oxo-2-propenyl]amino]-1-propanesulfonic acid partially or totally salified in the form of the ammonium salt, N,N-dimethylacrylamide and tetraethoxylated lauryl acrylate with trimethylolpropane triacrylate.

Polyacrylate crosspolymer-6 is a thickening and stabilizing polymer having a high associative behavior.

This polymer is generally in a powder form and prepared by a process comprising polymerization and precipitation steps.

As shown in the Working Examples, the presence of polyacrylate crosspolymer-6 in association with a crosslinked hyaluronic acid in a composition in accordance with the invention allows providing advantages in terms of stability compared to the presence of other associative anionic polymers such as high molecular weight crosslinked polyacrylic acid polymer (for example, Carbopol® Ultrez 10 marketed by Lubrizol) and mix of *Sclerotium* gum and xanthan gum (for example, Actigum™ marketed by Cargill).

The combination of polyacrylate crosspolymer-6 and crosslinked hyaluronic acid suitable for the present invention is very advantageous as explained below.

Indeed, this specific combination in a cosmetic composition in accordance with the invention:

provides good particles suspending properties to a composition in accordance with the invention, slowing or even avoiding sedimentation of said composition in accordance with the invention;

maintains the integrity of said composition in accordance with the invention even when said composition comprises a high amount of electrolytes;

does not alter the transparency of said composition in accordance with the invention;

avoid linting (or peeling) of said composition in accordance with the invention when it is topically applied on the skin;

allows said composition in accordance with the invention to resist to heating which occurs when, for example, such composition is sterilized by autoclaving;

possesses a toxicity which is acceptable for human beings.

As above-mentioned, polyacrylate crosspolymer-6 is applied topically in an efficient amount so as to obtain the desired effect(s).

A composition in accordance with the invention may comprise higher than 0.2% and lower than 1% by weight, preferably from about 0.5% to about 0.8% by weight, more preferably from about 0.5% to about 0.7%, of polyacrylate crosspolymer-6, relative to the total weight of the composition.

A composition in accordance with the invention may comprise a weight ratio polyacrylate crosspolymer-6/crosslinked hyaluronic acid ranging from about 0.3 to about 10, preferably from about 1.0 to about 4.0, more preferably from about 1.7 to about 2.8, still more preferably about 2 with respect to the total weight of the composition.

For example, among polyacrylate crosspolymer-6 or derivatives thereof suitable in a composition in accordance with the invention it may be cited the one marketed under the name of SEPIMAX ZEN™ by SEPPIC.

Hydroxyethylcellulose

A composition in accordance with the invention may further comprise an efficient amount of hydroxyethylcellulose.

For purpose of the present invention, the term "hydroxyethylcellulose" relates to a gelling and thickening agent derived from cellulose which is widely used in cosmetics. Further, this term includes hydroxyethylcellulose, its derivatives and mixtures thereof.

Advantageously, as shown in the Working Examples, the hydroxyethylcellulose provides a silky and rich touch to the composition in accordance with the invention and allows to increase the viscosity and the cross-over stress of the composition.

Hydroxyethylcellulose may be present in a composition in accordance with the invention in an amount ranging from about 0.1% to about 5% by weight, preferably from about 0.1% to about 2% by weight, more preferably from about 0.4% to about 1% by weight, still more preferably from about 0.5% to about 0.9% by weight, most preferably from about 0.6% to about 0.9% by weight relative to the total weight of said composition.

As hydroxyethylcellulose used in a composition in accordance with the invention it may be mentioned Natrosol™ 250 MR marketed by Ashland Company.

Thus, in a particular embodiment, a sterile and topical cosmetic composition in accordance with the present invention, comprises, in a physiologically acceptable medium, an efficient amount of crosslinked hyaluronic acid, an efficient amount of polyacrylate crosspolymer-6 and an efficient amount of hydroxyethylcellulose.

For the purpose of this invention an "efficient amount" in the expression "efficient amount of hydroxyethylcellulose" relates to the amount which is needed to provide a composition with desired viscosity, cross-over stress and texture while disclosing a rich feeling when applied on the skin surface to be cared.

The present disclosure also describes a sterile and topical cosmetic composition which comprises, in a physiologically acceptable medium, at least one crosslinked hyaluronic acid, at least one polyacrylate crosspolymer-6 and at least one hydroxyethylcellulose.

Additional Compounds

A composition in accordance with the invention may comprise, in addition to the efficient amount of crosslinked hyaluronic acid, the efficient amount of polyacrylate crosspolymer-6, and optionally the efficient amount of hydroxyethylcellulose, at least one additional compound compatible with use in sterile and topical cosmetic compositions.

Said at least one additional compound may be chosen by the one skilled in the art in view of the intended use of the cosmetic composition in accordance with the invention.

Additional compounds that may be used in the present invention can include antioxidants, amino acids, vitamins, minerals, nucleic acids, co-enzymes, chelating agents, water soluble solvent, any excipient commonly used in the technical field, such as for example copper sulfate, and mixtures thereof.

As an antioxidant, it may be mentioned glutathione, ellagic acid, spermine, resveratrol, retinol, L-carnitine, polyols, polyphenols, flavonols, theaflavins, catechins, caffeine, ubiquinol, ubiquinone, thioctic acid (also named α-lipoic acid) and mixture thereof.

As amino acid, it may be mentioned acetylcysteine (also named N-acetylcysteine or NAC), arginine, isoleucine, leucine, lysine, glycine, valine, threonine, proline, methionine, histidine, phenylalanine, tryptophan, and mixture thereof. Salts of amino acid may also be used such as lysine hydrochloride, as well as amino acids-mineral complexes such as copper lysinate and copper prolinate.

As vitamins it may be mentioned vitamins E, A, C, B including vitamins B6, B8, B4, B5, B9, B7 and B12, their derivatives such as pyridoxine and mixtures thereof.

As minerals, it may be mentioned zinc salts such as zinc acetate, magnesium salts, calcium salts, potassium salts, manganese salts, sodium salts, and mixtures thereof.

As nucleic acids, it may be mentioned adenosine, cytidine, guanosine, thymidine, their derivatives and mixture thereof.

As co-enzymes, it may be cited coenzyme Q10, CoA, NAD, NADP, and mixtures thereof.

The term "chelating agent" refers to an agent which is capable of complexing a metallic cation. Among chelating agents, it may be cited for example ethylenediamine tetraacetic acid (EDTA) and salts thereof (for example sodium or potassium salt).

The amounts of these additional compounds depend on several factors including their nature, the desired effect and the intended use of the composition in accordance with the invention.

In a composition in accordance with the invention, the total amount of additional compounds may range from about 0.1% to about 2% by weight, preferably from about 0.1 to about 0.5% by weight relative to the total weight of the composition.

The determination of these parameters falls within the general competence of the person skilled in the art.

As additional compound, the aqueous phase of the compositions in accordance with the invention may contain, besides water, one or more water soluble solvents at room temperature (25° C.). A soluble solvent may be for example a polyol with 2 to 20 carbon atoms or mixtures thereof.

For the purpose of the present invention, the term "polyol" should be understood to mean any organic molecule comprising at least two free hydroxyl groups.

A polyol suitable for the invention may be a compound such as a saturated or unsaturated, linear, branched or cyclic alkyl bearing, on its alkyl chain, at least two —OH functions, preferably at least three —OH-functions, and more preferably at least four —OH functions.

Among polyols, the following may be cited: un-crosslinked hyaluronic acid and its salts, glycerin, 1,3-propanediol, isoprene glycol, pentylene glycol, hexylene glycol, glycols such as ethylene glycol, propylene glycol, butylene glycol, diethylene glycol and dipropylene glycol, polyglycerols with 2 to 6 repeating units, for instance diglycerol, erythritol, arabitol, adonitol, sorbitol, mannitol, dulcitol, glucose, fructose, xylose, trehalose, sucrose, maltose, saccharose and lactose, and their derivatives such as for example methylglucoside phosphate and mixtures thereof.

According to a preferred embodiment, the one or more water soluble solvent(s) is (are) polyol(s). More preferably, the one or more water soluble solvent(s) is (are) polyol(s) which is(are) selected from glycerin, un-crosslinked hyaluronic acid or its salts and mixtures thereof. More preferably, the one or more water soluble solvent is (are) un-crosslinked hyaluronic acid and glycerin.

According to a particular embodiment, a composition in accordance with the invention further comprises at least one un-crosslinked hyaluronic acid or a salt thereof.

The term "non-crosslinked hyaluronic acid" is used interchangeably with the term "un-crosslinked hyaluronic acid" and it relates to the hyaluronic acid that was not submitted to a crosslinking reaction and which is optionally added to a composition in accordance to the invention. Non-crosslinked hyaluronic acid generally remains water soluble.

The non-crosslinked hyaluronic acid in accordance with the invention has preferably an average molecular weight ranging from about 1 000 Da to about 5 000 000 Da, preferably from about 5 000 Da to about 3 000 000 Da, more preferably from about 10 000 to about 1 000 000 Da.

The un-crosslinked hyaluronic acid used for preparing a composition in accordance with the invention may range from about 0% to about 20% by weight, preferably from about 0.2% to about 10% by weight, more preferably from about 0.5% to about 5% by weight relative to the total weight of the composition.

The non-crosslinked hyaluronic acid, when present in a composition in accordance with the invention, may be a hyaluronic acid salt chosen among hyaluronic acid physiologically acceptable salts such as the sodium salt, the potassium salt, the zinc salt, the silver salt and mixtures thereof.

One particularly preferred salt of non-crosslinked hyaluronic acid which can be used is sodium hyaluronate (NaHA).

Preferably, when present in a composition according to the invention, the un-crosslinked hyaluronic acid may be hydrolyzed. For example, it can be cited the one marketed under the name of Primalhyal® 50 by Solliance.

The term "hydrolyzed hyaluronic acid" refers to a hyaluronic acid crosslinked or un-crosslinked, which is allowed to cleave into fragments, for example after being treated with hydrogen peroxide and/or hyaluronidase, and/or after a prolonged exposure time in water.

When present, the amount of polyols in the composition of the invention may range, for example, from about 0.10% to about 0.50% by weight, preferably from about 0.20% to about 0.25% by weight relative to the total weight of the composition.

Typically, polyols have cosmetic activity acting as moisturizing agents that can provide better skin smoothness and skin moisture balance.

According to a particular embodiment, a composition according to the invention is devoid of preservatives.

According to a particular embodiment, said additional compound(s) is (are) dispersed into at least one balanced salt solution as defined above.

In one preferred embodiment, at least one additional compound comprised in a composition in accordance with the invention has on its own, that is to say without requiring any external agent to activate it, a cosmetic activity which may be in particular:

a photoprotective activity; and/or
a moisturizing or humectant activity; and/or
a desquamating activity; and/or
a soothing or anti-irritant activity; and/or
a anti-aging activity; and/or,
an anti-oxidant activity; and/or,
a regenerative activity; and/or,
a healing activity.

Such an additional compound may be for example a polyol, more particularly for example hyaluronic acid.

Further, such an additional compound, when present in a composition suitable for the invention can represent from about 0.000001% to about 20%, preferably from about 0.001% to about 10% and more preferably from about 0.01% to about 5% by weight relative to the total weight of the composition.

Of course, those skilled in the art will take care to choose this or these optional additional compounds and/or their quantities, such that the advantageous properties of the crosslinked hyaluronic acid and polyacrylate crosspolymer-6 in accordance with the invention are not, or substantially not, altered by the intended addition and that the properties of the resulting compositions are compatible with the topical route of administration.

Aqueous Composition

The composition in accordance with the invention may be an aqueous composition, i.e. it comprises mainly water.

Balanced Salt Solution

According to a particular embodiment, a composition in accordance with the invention may further comprise at least a balanced salt solution.

Preferably, said at least one balanced salt solution is a phosphate buffered saline, more preferably a $KH_2PO_4$/$K_2HPO_4$ saline buffer.

When present in a composition in accordance with the invention, said balanced salt solution is in an amount ranging from about 1% to about 20% by weight, preferably from about 5% to about 15% by weight, still more preferably from about 10% to about 13% by weight with respect to the total weight of the composition.

Composition in Accordance with the Invention

According to a particular embodiment, a composition in accordance with the invention made up of crosslinked hyaluronic acid may have a viscosity between about 1000 and about 4000 Cp (that is to say about 1 and about 4 Pa·s), preferably between about 1500 and about 2500 Cp (that is to say about 1.5 and about 2.5 Pa·s).

The viscosity of a composition in accordance with invention may be measured using a Brookfield type viscometer with a S93 mobile with a rotation speed of 50 rotations per minute (rpm), at 25° C.

According to a particular embodiment, a composition in accordance with the invention may have a complex viscosity $\eta^*$ of between about 2 Pa·s and about 8 Pa·s when measured at about 1 Hz.

The complex viscosity of a composition in accordance with the invention may be measured for a stress of 5 Pa, using a TA instrument DHR2 rheometer with a 1°/40 mm diameter cone-plate geometry.

According to a particular embodiment, a composition in accordance with the invention may have a cross-over stress of between about 5 and about 20 Pa.

The cross-over stress relates to the stress at which the value of G', the elastic modulus, decreases and equals the value of G", the viscous modulus (that is to say the cross between G' and G" values). In other words, the cross-over stress is the stress (in Pa) when G'=G". The stress and deformation strain at this point are those starting from which a material, predominantly elastic at the lower stresses and deformation strains, enters the flow region. This translates the destructuration of the gel, its cohesion. It may be measured using a rheometer with a cone-plate geometry. Alternatively, the measurements may also be carried out using a two-parallel rough plates geometry, which enables a better reliability and precision of cross-over measurements.

The cross-over measurement is carried out at 25° C., at a frequency of 1 Hz, with a stress sweep, using a TA instrument DHR2 rheometer with a 1°/40 mm diameter cone-plate geometry. G' and G" are recorded at an applied deformation stress of 5 Pa, i.e. in the viscoelasticity range where G' and G" remain stable. The value of the cross-over stress, ie. the stress when G' equals the viscous modulus G", is then also recorded.

According to a particular embodiment a composition in accordance with the invention comprises at least:
- a crosslinked hyaluronic acid, in particular a crosslinked hyaluronic acid gel;
- a polyacrylate crosspolymer-6; and
- water.

According to a particular embodiment a composition in accordance with the invention consists in:
- a crosslinked hyaluronic acid, in particular a crosslinked hyaluronic acid gel;
- a polyacrylate crosspolymer-6; and
- water.

According to a particular embodiment a composition in accordance with the invention comprises at least:
- a crosslinked hyaluronic acid, in particular a crosslinked hyaluronic acid gel;
- a polyacrylate crosspolymer-6;
- an un-crosslinked hyaluronic acid; and
- water.

According to a particular embodiment a composition in accordance with the invention consists in:
- a crosslinked hyaluronic acid, in particular a crosslinked hyaluronic acid gel;
- a polyacrylate crosspolymer-6;
- an un-crosslinked hyaluronic acid; and
- water.

According to a particular embodiment a composition in accordance with the invention comprises at least:
- a crosslinked hyaluronic acid, in particular a crosslinked hyaluronic acid gel;
- a polyacrylate crosspolymer-6;
- hydroxyethylcellulose; and
- water.

According to a particular embodiment a composition in accordance with the invention consists in:
- a crosslinked hyaluronic acid, in particular a crosslinked hyaluronic acid gel;
- a polyacrylate crosspolymer-6;
- hydroxyethylcellulose; and
- water.

According to a particular embodiment a composition in accordance with the invention comprises at least:
- a crosslinked hyaluronic acid, in particular a crosslinked hyaluronic acid gel;
- a polyacrylate crosspolymer-6;
- hydroxyethylcellulose;
- an un-crosslinked hyaluronic acid; and
- water.

According to a particular embodiment a composition in accordance with the invention consists in:
- a crosslinked hyaluronic acid, in particular a crosslinked hyaluronic acid gel;
- a polyacrylate crosspolymer-6;
- hydroxyethylcellulose;
- an un-crosslinked hyaluronic acid; and
- water.

According to another particular embodiment a composition in accordance with the invention comprises at least:
- between about 0.10% to about 0.60% by weight, preferably between about 0.20% to about 0.50% by weight, more preferably between about 0.25% to about 0.30% by weight, still more preferably between about 0.28% to about 0.29% by weight of crosslinked hyaluronic acid, with respect to the total weight of the composition; and
- from about 0.2% to about 1.0% by weight, preferably from about 0.5% to about 0.8% by weight, more preferably from about 0.5% to about 0.7% of polyacrylate crosspolymer-6, relative to the total weight of said composition According to another particular embodiment a composition in accordance with the invention consists in:
- between about 0.10% to about 0.60% by weight, preferably between about 0.20% to about 0.50% by weight, more preferably between about 0.25% to about 0.30/by weight, still more preferably between about 0.28% to about 0.29% by weight of crosslinked hyaluronic acid, with respect to the total weight of the composition; and
- from about 0.2% to about 1.0% by weight, preferably from about 0.5% to about 0.8% by weight, more preferably from about 0.5% to about 0.7% of polyacrylate crosspolymer-6, relative to the total weight of said composition; and
- water.

According to another particular embodiment a composition in accordance with the invention comprises at least:
- between about 5% to about 99.5% by weight, preferably between about 7% to about 50% by weight, more preferably between about 9% to about 20% by weight, still more preferably between about 10% to about 15% by weight of crosslinked hyaluronic acid gel with respect to the total weight of the composition, where said crosslinked hyaluronic acid gel comprises between about 10 mg/g and about 35 mg/g, preferably between about 15 mg/g and about 30 mg/g, still more preferably between about 20 mg/g and about 25 mg/g of total hyaluronic acid relative to the total weight of the crosslinked hyaluronic acid gel;
- from about 0.2% to about 1.0% by weight, preferably from about 0.5% to about 0.8% by weight, more preferably from about 0.5% to about 0.7% of polyacrylate crosspolymer-6, relative to the total weight of said composition; and
- water.

According to another particular embodiment a composition in accordance with the invention consists in:
- between about 5% to about 99.5% by weight, preferably between about 7% to about 50% by weight, more preferably between about 9% to about 20% by weight, still more preferably between about 10% to about 15% by weight of crosslinked hyaluronic acid gel with respect to the total weight of the composition, where said crosslinked hyaluronic acid gel comprises between about 10 mg/g and about 35 mg/g, preferably between about 15 mg/g and about 30 mg/g, still more preferably between about 20 mg/g and about 25 mg/g of total hyaluronic acid relative to the total weight of the crosslinked hyaluronic acid gel;
- from about 0.20% to about 1.00% by weight, preferably from about 0.5% to about 0.8% by weight, more preferably from about 0.5% to about 0.7% of polyacrylate crosspolymer-6, relative to the total weight of said composition; and
- water.

In a preferred embodiment, a composition in accordance with the invention comprises at least:
- a crosslinked hyaluronic acid and/or a salt thereof;
- a polyacrylate crosspolymer-6;
- an un-crosslinked hyaluronic acid and/or a salt thereof;
- water;
- polyols;
- minerals;
- aminoacids;
- chelating agents;

phosphate buffer saline;
antioxidants; and
monosaccharides phosphate.

In a preferred embodiment, a composition in accordance with the invention consists in:
a crosslinked hyaluronic acid and/or a salt thereof;
a polyacrylate crosspolymer-6;
an un-crosslinked hyaluronic acid and/or a salt thereof;
water;
polyols;
minerals;
aminoacids;
chelating agents;
phosphate buffer saline;
antioxidants; and
monosaccharides phosphate.

In a particularly preferred embodiment, a composition in accordance with the invention comprises at least:
a crosslinked hyaluronic acid and/or a salt thereof;
a polyacrylate crosspolymer-6;
hydroxyethylcellulose;
an un-crosslinked hyaluronic acid and/or a salt thereof;
water;
polyols;
minerals;
aminoacids;
chelating agents;
phosphate buffer saline;
antioxidants; and
monosaccharides phosphate.

In a particularly preferred embodiment, a composition in accordance with the invention consists in:
a crosslinked hyaluronic acid and/or a salt thereof;
a polyacrylate crosspolymer-6;
hydroxyethylcellulose;
an un-crosslinked hyaluronic acid and/or a salt thereof;
water;
polyols;
minerals;
aminoacids;
chelating agents;
phosphate buffer saline;
antioxidants; and
monosaccharides phosphate.

Of course, those skilled in the art will take care to choose the amount of each component comprised in a composition in accordance with the invention so as to obtain a total sum of the amounts equal to 100% by weight with respect to the total weight of the composition.

Method for Preparing a Sterile Composition in Accordance with the Invention

A sterile cosmetic composition in accordance with the invention may be prepared by any process known by the skilled person.

Advantageously, a sterile cosmetic composition in accordance with the invention may be obtained by a process comprising at least the steps of:
a) providing an aqueous phase optionally comprising chelating agents;
b) heating said aqueous phase at a temperature ranging from about 10° C. to about 65° C.;
c) adding to said aqueous phase the efficient amount of polyacrylate crosspolymer-6 and, when applicable, the hydroxyethylcellulose and/or a un-crosslinked hyaluronic acid or salts thereof, while homogenizing by stirring with a homogenizer until complete solubilization;
d) adding the efficient amount of crosslinked hyaluronic acid while homogenizing by stirring in the homogenizer until complete solubilization;
e) when applicable, cooling at a temperature ranging from about 10° C. to about 35° C., and adding the additional compounds as defined above under simple stirring;
where said simple stirring may be executed by a manual and/or a mechanical stirring.

In a particular embodiment, the homogenization time in step c) is comprised between from about 1 min to about 60 min preferably from about 5 min to about 30 min and still more preferably during about 15 min.

In another particular embodiment, the homogenization time in step d) is comprised between from about 1 min to about 60 min, preferably from about 5 min to about 30 min and still more preferably during about 15 min.

The heating in step b) of a process in accordance with the invention may be carried out at a temperature ranging from about 15° C. to about 80° C., preferably from about 20° C. to about 70° C., more preferably from about 25° C. to about 65° C.

According to a first embodiment, the polyacrylate crosspolymer-6 and, when applicable, the hydroxyethylcellulose and/or an un-crosslinked hyaluronic acid which are added in the step c) of a process in accordance with the invention, are in powder and/or fiber form.

According to a second embodiment, the polyacrylate crosspolymer-6 and, when applicable, the hydroxyethylcellulose and/or an un-crosslinked hyaluronic acid which are added in the step c) of a process in accordance with the invention, are in liquid and/or gel form, i.e. preliminary solubilized.

The duration of the stirring in the homogenizing steps c) and d) has been determined and optimized so as to obtain an appropriate average particle size in accordance with the dosage form of a composition according to the invention.

The homogenization is considered to be satisfactory when the composition obtained has a homogeneous colouration, no agglomerate and a uniform viscosity.

According to a particular embodiment, the homogenizing of steps c) and d) are each performed by stirring in a homogenizer until complete solubilisation during about 15 min.

The homogenizing steps c), and d) may be carried out by one or several conventional mean(s) which may be chosen by one skilled in the art. In particular the homogenization may be performed by stirring in an ULTRA-TURRAX® homogenizer marketed by IKA or a rotor-stator SILVERSON or a POLYTRON.

The cooling step in step e) may be carried out at a temperature ranging from about 5° C. to about 60° C., more preferably from about 10° C. to about 45° C. still more preferably from about 20 to about 35° C.

The simple stirring in step e) may be a manual and/or a mechanical stirring.

For purpose of the present invention:
the term "simple stirring" refers to a process for preparing a mixture comprising at least two components by vortex agitation;
the term "manual stirring" refers to a process for stirring which does not involve any engine operation, i.e. stirring with a spatula;
the term "mechanical siring" refers to a process for stirring involving at least an operation with an engine e.g. stirring with a magnetic agitator.

Administration of the Composition

A composition in accordance with the invention is suitable for topical administration.

It can be in any form conventionally used for topical application.

A composition suitable for the invention may be in the form of a soft, semi-solid or solid consistency cream or in the form of a gel advantageously an aqueous gel which may be obtained by dispersing an aqueous phase in an aqueous phase In a preferred embodiment, a composition in accordance with the invention is in the form of an aqueous gel.

More particularly, the composition is an aqueous dispersion in an aqueous phase.

Packaging of the Composition

The composition may be packaged in any packaging which is conventionally used in the cosmetic field for topical compositions, in particular in sterile packaging.

For the storage of a composition in accordance with the invention in a sterile environment, the packaging is preferably chosen among suitable multi-dose or single-dose packaging.

Thus, according to a first embodiment, said packaging is scored so as to allow said composition to be topically administered.

For example, said packaging may be in the form of a single-dose capsule or vial, which has a scored end.

According to a second embodiment, said packaging has a seal which allows hermetic closing during storage and which can be opened at the time of use.

According to a preferred embodiment, a composition in accordance with the invention is packaged in a single-dose sterile reservoir such as a capsule or a vial.

Advantageously, the single-dose form allows ensuring the sterility of a composition in accordance with the invention before its application onto the skin.

More particularly, the volume of said reservoir is comprised between about 1 ml and about 10 ml, more preferably between about 2 ml and about 5 ml and still more preferably is about 4 ml.

According to a preferred embodiment, a composition in accordance with the invention is formulated in the form of a dispersion within the packaging.

Cosmetic Process

As mentioned above, the present invention also relates to a cosmetic process for caring the skin comprising at least the step of applying topically, on one or more surface(s) of the skin to be cared, an effective amount of a sterile and topical cosmetic composition as defined above, to a subject who has previously been subjected to one or more aesthetic and/or cosmetic intervention(s) such as injection of a dermal filler composition, injection of botulinum toxin, peeling (e.g. chemical peeling), micro-needling, mesotherapy, lipo-filling, injection of platelet-rich human plasma, radiofrequency, dermabrasion and lasers use.

According to a preferred embodiment, the subject was previously subjected to one or more micro-needling procedure(s).

The above-mentioned aesthetic and/or cosmetic intervention(s) can be carried out using any of the known methods in the art.

For example, a dermal filler may be administered by means of an injection device suitable for intra-epidermal and/or intra-dermal and/or subcutaneous injection.

The injection device, notably when the dermal filler is administered by means of an injection device suitable for intra-epidermal and/or intra-dermal and/or subcutaneous injection, may be selected among syringes, sets of micro-syringes, laser device, hydraulic device, injection gun, needleless device, roller with microneedles.

According to a particular embodiment, the aesthetic and/or cosmetic intervention is an injection of a dermal filler composition. According to this embodiment, the injectable dermal filler composition may be a biodegradable and biocompatible material such as crosslinked and/or non-crosslinked collagen, crosslinked and/or non-crosslinked hyaluronic acid, calcium hydroxylapatite, and poly-L-lactic acid (PLLA).

According to an embodiment, a sterile and topical cosmetic composition in accordance with the invention may be applied between two identical aesthetic or cosmetic interventions chosen among those defined above.

According to this embodiment, a composition in accordance with the invention may be topically applied after, for example:
- a cosmetic injection of a cosmetic injectable crosslinked hyaluronic acid but before a subsequent cosmetic injection of the same crosslinked hyaluronic acid, or
- a cosmetic injection of a cosmetic injectable un-crosslinked collagen but before a subsequent cosmetic injection of the same cosmetic injectable un-crosslinked collagen, or
- a cosmetic injection of a Botulinum toxin but before a subsequent cosmetic injection of the same Botulinum toxin, or
- a micro-needling but before a subsequent micro-needling, or
- a mesotherapy of an injectable product but before a subsequent mesotherapy of the same injectable product, or
- a lipo-filling but before a subsequent lipo-filling,
- an injection of platelet-rich human plasma but before a subsequent injection of platelet-rich human plasma, or
- etc.

According to another embodiment, the sterile and topical cosmetic composition in accordance with the invention may be applied between two different aesthetic or cosmetic interventions as defined above.

According to this embodiment, a composition in accordance with the invention may be topically applied after, for example:
- a cosmetic injection of a cosmetic injectable crosslinked hyaluronic acid but before a subsequent cosmetic injection of a different crosslinked hyaluronic acid, or
- a cosmetic injection of a cosmetic injectable crosslinked hyaluronic acid but before a subsequent cosmetic injection of an un-crosslinked hyaluronic acid, or
- a cosmetic injection of a cosmetic injectable crosslinked hyaluronic but before a subsequent cosmetic injection of a cosmetic injectable un-crosslinked collagen, or
- a cosmetic injection of a Botulinum toxin but before a subsequent cosmetic injection of an injectable crosslinked hyaluronic, or
- a micro-needling but before a subsequent injectable crosslinked hyaluronic acid, or
- a cosmetic injection of a cosmetic injectable crosslinked hyaluronic acid but before a subsequent mesotherapy, or
- a mesotherapy but before a subsequent lipo-filling,
- an injection of platelet-rich human plasma but before a subsequent injection of a cosmetic injectable crosslinked hyaluronic, or
- etc.

According to another embodiment, the sterile and topical cosmetic composition in accordance with the invention may be applied after one or more aesthetic and/or cosmetic intervention(s) as those defined above while no other subsequent aesthetic and/or cosmetic intervention such as those defined above be carried out.

A sterile and topical cosmetic composition in accordance with the invention may be applied to the one or more skin surface(s) to be cared.

A sterile and topical cosmetic composition in accordance with the invention may be applied within one hour following the end of the one or more previous aesthetic and/or cosmetic intervention(s) and until one month after the end of the one or more previous aesthetic and/or cosmetic intervention(s). Preferably, a sterile and topical cosmetic composition in accordance with the invention is applied within one hour following the end of the one or more previous aesthetic and/or cosmetic intervention(s).

A sterile and topical cosmetic composition in accordance with the invention may be applied to the one or more skin surface(s) to be cared once, one or more time(s) daily, one or more time(s) weekly or one or more time(s) monthly preferably, said composition is applied once after the one or more previous aesthetic and/or cosmetic intervention(s).

According to a preferred embodiment, a sterile and topical cosmetic composition in accordance with the invention is applied once after the one or more previous aesthetic and/or cosmetic intervention(s).

A sterile and topical cosmetic composition in accordance with the invention may be applied to the one or more skin surface(s) to be cared, in particular for an unlimited duration.

Advantageously, a composition in accordance with the invention may allow enhancing, extending and/or accelerating the cosmetic effects associated with the one or more aesthetic and/or cosmetic intervention(s) such as those described above.

Among said cosmetic effects, it may be cited anti-wrinkle effect, anti-scar effect, anti-stretch marks effect, retightening effect, lifting effect of sagged skin.

Advantageously, the use of a sterile and topical composition in accordance with the invention may allow to diminish the frequency of the aesthetic and/or cosmetic interventions such as those described above that is to say to space the aesthetic and/or cosmetic interventions repetition in time, and even replace such interventions in certain cases.

Advantageously, the use of a sterile and topical composition in accordance with the invention may replace subsequent aesthetic and/or cosmetic interventions such as those described above.

The use of a sterile and topical composition in accordance with the invention allows to improve the quality of the skin and/or helps the restoration of the skin's barrier, if necessary, after one or more previous and/or cosmetic intervention(s) such as injection of a dermal filler composition, injection of botulinum toxin, peeling (e.g. chemical peeling), micro-needling, mesotherapy, lipo-filling, injection of platelet-rich human plasma, radiofrequency, dermabrasion and lasers use.

According to a particular embodiment, a process in accordance with the invention further results in an enhanced and/or accelerated healing/caring of the skin tissue at the surface(s) of the one or more previous aesthetic and/or cosmetic intervention(s) such as injection of a dermal filler composition, injection of botulinum toxin, peeling (e.g. chemical peeling), micro-needling, mesotherapy, lipo-filling, injection of platelet-rich human plasma, radiofrequency, dermabrasion and lasers use. According to a preferred embodiment, the subject was previously subjected to one or more micro-needling procedure(s).

According to another particular embodiment, a process in accordance with the invention further avoids the extent of one or more commonly occurring adverse side effects associated with aesthetic and/or cosmetic intervention(s) such as injection of a dermal filler composition, injection of botulinum toxin, peeling (e.g. chemical peeling), micro-needling, mesotherapy, lipo-filling, injection of platelet-rich human plasma, radiofrequency, dermabrasion and lasers use. According to a preferred embodiment, the subject was previously subjected to one or more micro-needling procedure(s). Side effects which may be observed include oedemas, bruising, bleeding, discomfort, infection, persistent or temporary swelling, redness, itching, erythema, sensitivity, localized pallor, irregularities, small hematomas, acute or chronic inflammatory reactions, abscesses, headache, paraesthesia, nausea, facial pain and granulomatous reactions. These reactions are located at and/or close to the skin surface(s) of the subject which was(were) cared with an aesthetic and/or cosmetic intervention.

According to a variant, the skin can be treated with a different composition, not covered by the invention, after topical administration of a composition in accordance with the invention. Said composition which may be posteriorly applied to the skin may be, for example, a makeup composition and/or another skin care composition.

Throughout the description, including the claims, the expression "comprising a" should be understood as being synonymous with "comprising at least one" unless specifically stated otherwise.

The expressions "between . . . and . . . " and "ranging from . . . to . . . " should be understood to mean that the limits are inclusive, unless specified otherwise.

The invention is illustrated in greater details by the examples in accordance with the invention described below.

Unless otherwise mentioned, the amounts indicated are expressed as mass (weight) percentages of active material.

Working Examples

Materials and Methods:
Viscosity Measurement
The viscosity of a composition in accordance with invention may be measured using a Brookfield type viscometer with a S93 mobile with a rotation speed of 50 rotations per minute (rpm), at 25° C.

The complex viscosity (Pa·s) of a composition in accordance with the invention may be measured using a TA instrument DHR2 rheometer with a 1°/40 mm diameter cone-plate geometry at a stress of 5 Pa, at 25° C.

Cross Over Stress Determination
The cross-over stress measurement is carried out at 25° C., at a frequency of 1 Hz, with a stress sweep, using a TA instrument DHR2 rheometer with a 1°/40 mm diameter cone-plate geometry. G' and G" are recorded at an applied deformation stress of Pa, i.e. in the viscoelasticity range where G' and G" remain stable. The value of the cross-over stress, i.e. when G' decreases to equal the viscous modulus G", is then also recorded.

Stability Determination
In the following examples, stability of a composition is established when it maintains its homogeneity over time. Homogeneity of samples of studied compositions were determined after storage at ambient temperature during 2 months and after subjected to an accelerated aging by exposition to extreme conditions, i.e. at a temperature of 50° C. during 2 months.

Homogeneity Determination

The homogenization is considered to be satisfactory when the composition obtained has a homogeneous colouration, no agglomerate and a uniform viscosity.

In the following examples, homogeneity of a composition is determined by measuring its rheological properties, such as its complex viscosity (Pa·s, 1 Hz), at different point of its storage pot, i.e. by sampling composition on the top and the bottom of the pot, said composition being previously stored vertically on a shelf at ambient temperature.

The difference of complex viscosities (Pa·s, 1 Hz) between the top and the bottom of the pot is calculated ($|\Delta|$ (top/bottom) of complex viscosity (Pa·s, 1 Hz)). More the variation is important, more the composition is heterogeneous.

A composition is considered as being stable up to a difference of complex viscosities (Pa·s, 1 Hz) of 5%.

Organoleptic Properties

Transparency and Bubbles Assessment

The transparency and the presence of bubbles in the below-mentioned samples are qualitatively assessed by visual inspection.

Texture Evaluation

For evaluating the texture of the below mentioned compositions, ten persons have blind tested each composition and answered a survey composed of ten questions about the characterization of their texture. The survey included the following questions: Does the composition have a grainy texture? Is it easy to spread on the skin? Does the film forming sensation remain on the cared skin surface? etc. . . . .

Reparation of the Skin Barrier

The efficacy of a composition in accordance with the invention in restoring the cutaneous barrier is evaluated by comparing the Trans-Epidermal Water Loss (TEWL) between a damaged skin surface treated with a composition in accordance with the invention and a non-treated damaged skin surface.

TEWL Measurements

TEWL measurements were taken under temperature and relative humidity controlled conditions, as follows: temperature=22±2° C. and relative humidity=501 10%.

TEWL was measured using a Tewameter® TM 300 (Courage+Khazaka, electronic GmbH). The following equation which represents the Diffusion law (discovered By Adolf Fick in 1855) is the basis for the measurement:

$$\frac{dm}{dt} = -D \times A \times \frac{dp}{dx}$$

where: A=surface in $m^2$; water transported (in g); time (h); diffusion constant (=0.0877 g/mhmm Hg); vapor pressure of the atmosphere (mm Hg); distance from skin surface to point of measurement (m).

The diffusion flow dm/dt indicates the mass per $cm^2$ which is transported in a specific period of time. It is proportional to the area A and the change of concentration per distance (dp/dx). D is the diffusion coefficient of water vapor in the air. This law is only valid within a homogenous diffusion zone, which is approximately formed by a hollow cylinder. The resulting density gradient is measured indirectly by two pairs of sensors (temperature and relative humidity) and is analyzed by a microprocessor. The measuring head of the probe is a narrow hollow cylinder (10 mm diameter and 20 mm height), in order to minimize influences of air turbulence inside the probe.

The Study Protocol

The study was carried out on 20 healthy subjects (female and male) aged between 18 and 65 years old.

First, two skin surfaces on each volunteers back were selected. The TEWL of these surfaces were measured for each subject and determine as the baseline value (T-1).

Then the two selected surfaces were treated by applying a patch test containing a water solution of Sodium Lauryl Sulfate at 2% in order to induce an alteration of the skin barrier function during 24 hours. Then patches were removed and one of the two selected site of each subject was treated with a composition in accordance with the invention.

The TEWL of all selected surfaces were measured at 15 (T15 min), 30 (T30 min), 60 (T60 min) and 120 (T120 min) minutes after the application of the composition in accordance with the invention.

Example 1: Composition in Accordance with the Invention

A composition (composition 1) in accordance with the invention comprises the components as shown in Table 1 and was prepared as described below.

TABLE 1

| Phases | Components - INCI names | Composition 1 % by weight |
|---|---|---|
| A | WATER | QSP |
| A | DISODIUM EDTA marketed under Dissolvine NA2 ® by AkzoNobel | 0.100000 |
| B | HYDROLYZED HYALURONIC ACID marketed under PRIMALHYAL ® 50 by Solliance | 1.000000 |
| B | HYDROXYETHYLCELLULOSE marketed under NATROSOL Natrosol ™ 250 MR by Ashland | 0.800000 |
| B | POLYACRYLATE CROSSPOLYMER-6 marketed under the name of SEPIMAX ™ ZEN by SEPPIC Company | 0.600000 |
| C | PHOSPHATE BUFFER SALINE | 12.712442 |
| C | SODIUM HYALURONATE CROSSPOLYMER-2 | 0.287500 |
| D | GLYCERIN | 0.250000 |
| D | METHYLGLUCOSIDE PHOSPHATE | 0.025000 |
| D | COPPER LYSINATE/PROLINATE | 0.012500 |
| E | GLUTATHIONE | 0.000010 |
| E | PYRIDOXINE HCl | 0.000010 |
| E | THIOCTIC ACID | 0.000010 |
| E | ACETYL CYSTEINE | 0.000005 |
| E | LYSINE HYDROCHLORIDE | 0.000005 |
| E | VALINE | 0.000004 |
| E | ARGININE | 0.000002 |
| E | GLYCINE | 0.000002 |
| E | ISOLEUCINE | 0.000002 |
| E | LEUCINE | 0.000002 |
| E | THREONINE | 0.000002 |
| E | ZINC ACETATE | 0.000002 |
| E | PROLINE | 0.000001 |
| E | COPPER SULFATE | 0.00000033 |

Composition 1 in accordance with the invention was prepared by the following process:
1) heating phase A at 65° C. until disodium EDTA is well dissolved;
2) adding ingredients of phase B in powder form to phase A under homogenization with ULTRA-TURRAX® homogenizer marketed by IKA;

3) homogenizing until complete solubilization (about 15 min);

4) adding phase C under homogenization with ULTRA-TURRAX® homogenizer marketed by IKA;

5) homogenizing until complete solubilization (about 15 min);

6) cooling at 35° C. and then adding phase D under simple stirring;

7) adding the ingredients of phase E under simple stirring;

8) cooling at 25° C.;

where said simple stirring was a mechanical stirring as defined above.

The thus obtained composition is in the form of a transparent aqueous gel.

Finally, composition 1 in accordance with the invention was filled into a monodose vial.

Example 2: Repairing Skin Barrier by a Composition in Accordance with the Invention The repairing effect of the composition 1 of example 1 in accordance with the invention was tested according to the protocol as described above.

The results are reported in the FIG. 1 and in the Table 2 below.

TABLE 2

| Time | | T −1 | T15 min | T30 min | T60 min | T120 min |
|---|---|---|---|---|---|---|
| TEWL (g/h/m$^2$) | Treated skin | 9.08 | 53.32 | 45.63 | 40.57 | 40.53 |
| | Untreated skin | 8.96 | 53.53 | 52.1 | 49.27 | 48.94 |

In view of the results and of the FIG. 1, it comes out that after its applying on the skin surface, the composition 1 in accordance with the invention promotes a faster restoration of the skin barrier function as demonstrated by the TEWL % variations between the treated and untreated skin surface. The reduction of the TEWL after alteration of the skin is significantly higher for skin surface treated than for the untreated surface at each experimental monitored time.

Thus, the quality of the skin is improved after the applying on the skin surface of the composition 1 in accordance with the invention.

Example 3: Impact of the Use of Crosslinked Hyaluronic Acid Versus the Use of Un-Crosslinked Hyaluronic Acid The composition 1 of example 1, in accordance with the invention, was compared with a composition (composition 2) in which the crosslinked hyaluronic acid gel was replaced with an un-crosslinked hyaluronic acid solution.

The composition 2 was prepared according to the same process of preparation as the one for the composition 1 in accordance with the invention, as explained in example 1.

The composition 2 comprises the components as shown in Table 3 below.

The un-crosslinked hyaluronic acid solution was prepared by dissolving hyaluronic acid fibers within a phosphate buffer solution.

TABLE 3

| Phases | Components - INCI names | Composition 2 % by weight |
|---|---|---|
| A | WATER | QSP |
| A | DISODIUM EDTA marketed under Dissolvine NA2 ® by AkzoNobel | 0.100000 |
| B | HYDROLYZED HYALURONIC ACID marketed under PRIMALHYAL ® 50 by Solliance | 1.000000 |
| B | HYDROXYETHYLCELLULOSE marketed under NATROSOL Natrosol ™ 250 MR by Ashland | 0.800000 |
| B | POLYACRYLATE CROSSPOLYMER-6 marketed under the name of SEPIMAX ™ ZEN by SEPPIC Company | 0.600000 |
| C | PHOSPHATE BUFFER SALINE | 12.712442 |
| C | UN-CROSSLINKED HYALURONIC ACID | 0.287500 |
| D | GLYCERIN | 0.250000 |
| D | METHYLGLUCOSIDE PHOSPHATE | 0.025000 |
| D | COPPER LYSINATE/PROLINATE | 0.012500 |
| E | GLUTATHIONE | 0.000010 |
| E | PYRIDOXINE HCl | 0.000010 |
| E | THIOCTIC ACID | 0.000010 |
| E | ACETYL CYSTEINE | 0.000005 |
| E | LYSINE HYDROCHLORIDE | 0.000005 |
| E | VALINE | 0.000004 |
| E | ARGININE | 0.000002 |
| E | GLYCINE | 0.000002 |
| E | ISOLEUCINE | 0.000002 |
| E | LEUCINE | 0.000002 |
| E | THREONINE | 0.000002 |
| E | ZINC ACETATE | 0.000002 |
| E | PROLINE | 0.000001 |
| E | COPPER SULFATE | 0.00000033 |

It comes out from visual control of the compositions 1 and 2 that the combination of un-crosslinked hyaluronic acid and polyacrylate crosspolymer-6 provides a more liquid and less filmogenic composition than the combination of crosslinked hyaluronic acid and polyacrylate crosspolymer-6 which provides a composition (composition 1) in accordance with the invention which is a semi-solid and film-forming aqueous gel.

Moreover, the stability of compositions 1 and 2 was assessed by comparison of their complex viscosities after a storage under heat (2 months, 50° C.) and a storage at room temperature (2 months, 25° C.). The results are presented in the Table 4 here below.

TABLE 4

| Compositions | Difference of complex viscosity (\| η* at 50° C. − η* at 25° C. \|) (Pa · s, 1 Hz) |
|---|---|
| 1 | −60.1 |
| 2 | −75.4 |

In view of this results, a composition in accordance with the invention (composition 1) comprising a crosslinked hyaluronic acid is more stable than a composition comprising an un-crosslinked hyaluronic acid (composition 2) instead of a crosslinked hyaluronic acid, the composition 2 disclosing a greater decrease of complex viscosity after storage under heat.

Further, the complex viscosity and the cross-over stress of compositions 1 and 2 were measured according to the methods explained here above. The results are presented here below in Table 5.

TABLE 5

| Compositions | Complex viscosity (η*, Pa · s, 1 Hz) | Cross-over stress (τ, Pa, 1 Hz) |
|---|---|---|
| 1 | 5.2 | 11.5 |
| 2 | 3.8 | N/A |

As stated above, the cross-over stress of a viscoelastic composition represents the deformation stress at which the composition starts to flow and become more liquid than solid. The higher it is, the higher is the structural resistance of the composition and its ability to resist flowing. The composition 2 comprising an un-crosslinked hyaluronic acid is so much fluid that it does not present any cross-over stress when measured at 1 Hz.

These results are consistent with the visual and touching inspection of compositions 1 and 2, as composition 1 has a viscosity and a cross-over stress greater than composition 2 and discloses a thicker and more filmogenic texture than composition 2.

In conclusion, in addition to the improvement of the texture of the composition, the use of a crosslinked hyaluronic acid allows the preparation of a composition in accordance with the invention more stable under heat in comparison with a composition comprising an un-cross-linked hyaluronic acid.

Example 4: Impact of the Use of Polyacrylate Crosspolymer-6 as a Thickener in a Composition in Accordance with the Invention Versus the Use of Carbopol® Ultrez 10 or Actigum™

The composition 1 in accordance with the invention was compared with two others compositions (compositions 3 and 4) in which instead of polyacrylate crosspolymer-6 other associative anionic polymers were used as thickeners, respectively Carbopol® Ultrez 10 (high molecular weight, crosslinked polyacrylic acid polymer) marketed by Lubrizol and Actigum™ VSX 20 (mix of *Sclerotium* gum and xanthan gum) marketed by Cargill.

The compositions 3 and 4 were prepared according to the same process of preparation as the one for the composition 1 in accordance with the invention, as explained in example 1.

The compositions 3 and 4 comprise the components as shown in Table 6 below.

TABLE 6

| Phases | Components - INCI names | Composition 3 % by weight | Composition 4 % by weight |
|---|---|---|---|
| A | WATER | QSP | QSP |
| A | DISODIUM EDTA marketed under Dissolvine NA2 ® by AkzoNobel | 0.100000 | 0.100000 |
| B | HYDROLYZED HYALURONIC ACID marketed under PRIMALHYAL ® 50 by Solliance | 1.000000 | 1.000000 |
| B | HYDROXYETHYLCELLULOSE marketed under NATROSOL Natrosol ™ 250 MR by Ashland | 0.800000 | 0.800000 |
| B | MIX OF SCLEROTIUM GUM AND XANTHAN GUM marketed under Actigum ™ VSX 20 by Cargill | — | 0.600000 |
| B | HIGH MOLECULAR WEIGHT, CROSSLINKED POLYACRYLIC ACID POLYMER marketed under Carbopol ® Ultrez 10 by Lubrizol | 0.600000 | — |
| C | PHOSPHATE BUFFER SALINE | 12.712442 | 12.712442 |
| C | SODIUM HYALURONATE CROSSPOLYMER-2 | 0.287500 | 0.287500 |
| D | GLYCERIN | 0.250000 | 0.250000 |
| D | METHYLGLUCOSIDE PHOSPHATE | 0.025000 | 0.025000 |
| D | COPPER LYSINATE/PROLINATE | 0.012500 | 0.012500 |
| E | GLUTATHIONE | 0.000010 | 0.000010 |
| E | PYRIDOXINE HCl | 0.000010 | 0.000010 |
| E | THIOCTIC ACID | 0.000010 | 0.000010 |
| E | ACETYL CYSTEINE | 0.000005 | 0.000005 |
| E | LYSINE HYDROCHLORIDE | 0.000005 | 0.000005 |
| E | VALINE | 0.000004 | 0.000004 |
| E | ARGININE | 0.000002 | 0.000002 |
| E | GLYCINE | 0.000002 | 0.000002 |
| E | ISOLEUCINE | 0.000002 | 0.000002 |
| E | LEUCINE | 0.000002 | 0.000002 |
| E | THREONINE | 0.000002 | 0.000002 |
| E | ZINC ACETATE | 0.000002 | 0.000002 |
| E | PROLINE | 0.000001 | 0.000001 |
| E | COPPER SULFATE | 0.00000033 | 0.00000033 |

The viscosity and some organoleptic properties of the compositions 1, 3 and 4 were determined and the corresponding results are summarized in Table 7 below.

TABLE 7

| Compositions | Thickeners | Complex viscosity (Pa · s, 1 Hz) | Cross-over stress (Pa, 1Hz) | \|Δ\| (top/bottom) of complex viscosity (Pa · s, 1 Hz) | Transparency |
|---|---|---|---|---|---|
| 1 | Polyacrylate crosspolymer-6 | 5.2 | 11.6 | 4.3 | Yes |
| 3 | High molecular weight, crosslinked polyacrylic acid polymer marketed under Carbopol ® Ultrez 10 by Lubrizol | 9.2 | 14.7 | 0.2 | Yes |
| 4 | Mix of sclerotium gum and xanthan gum marketed under Actigum ™ VSX 20 by Cargill | 9.6 | 30.7 | 5.5 | No |

Composition 1 in accordance with the invention and composition 3 are homogeneous (|Δ|(top/bottom) of complex viscosity less than 5%) whereas composition 4 does not disclose enough homogeneity (|Δ|>5%).

Further, composition 4 is not transparent and discloses a too high cross-over stress traducing its difficulties for flowing and its important cohesion, such characteristics making it a product which is not conform for the purpose of the present invention.

Composition 3 has desired mechanical properties and homogeneity such as composition 1 but its texture is less pleasant and does not leave a film-forming sensation after its application. This notably emerges from the texture evaluation where only 22% of the persons questioned quite agree that the composition 3 leaves a film-forming sensation on the skin whereas 100% of the persons questioned strongly agree that the composition 1 leaves a pleasant film on the skin.

These results demonstrate that only the composition 1, in accordance with the invention, shows the suitable combination of appearance, texture, homogeneity and viscosity parameters whereas other associative anionic polymers failed attaining such a combination of properties.

Example 5: Impact of the Amount of Polyacrylate Crosspolymer-6 Used in a Composition in Accordance with the Invention Composition 1 in accordance with the invention was compared with two other compositions (compositions 5 and 6), which comprise respectively 0.2% by weight and 1% by weight of polyacrylate crosspolymer-6 instead of 0.6% by weight used in composition 1, with respect to the total weight of the composition.

The compositions 5 and 6 were prepared according to the same process of preparation as the one for the composition 1 in accordance with the invention, as explained in example 1.

The compositions 5 and 6 comprise the components as shown in Table 8 below,

TABLE 8

| Phases | Components - INCI names | Composition 5 % by weight | Composition 6 % by weight |
|---|---|---|---|
| A | WATER | QSP | QSP |
| A | DISODIUM EDTA marketed under Dissolvine NA2 ® by AkzoNobel | 0.100000 | 0.100000 |
| B | HYDROLYZED HYALURONIC ACID marketed under PRIMALHYAL ® 50 by Solliance | 1.000000 | 1.000000 |
| B | HYDROXYETHYLCELLULOSE marketed under NATROSOL Natrosol ™ 250 MR by Ashland | 0.800000 | 0.800000 |

TABLE 8-continued

| Phases | Components - INCI names | Composition 5 % by weight | Composition 6 % by weight |
|---|---|---|---|
| B | POLYACRYLATE CROSSPOLYMER-6 marketed under the name of SEPIMAX ™ ZEN by SEPPIC Company | 0.200000 | 1.000000 |
| C | PHOSPHATE BUFFER SALINE | 12.712442 | 12.712442 |
| C | SODIUM HYALURONATE CROSSPOLYMER-2 | 0.287500 | 0.287500 |
| D | GLYCERIN | 0.250000 | 0.250000 |
| D | METHYLGLUCOSIDE PHOSPHATE | 0.025000 | 0.025000 |
| D | COPPER LYSINATE/PROLINATE | 0.012500 | 0.012500 |
| E | GLUTATHIONE | 0.000010 | 0.000010 |
| E | PYRIDOXINE HCl | 0.000010 | 0.000010 |
| E | THIOCTIC ACID | 0.000010 | 0.000010 |
| E | ACETYL CYSTEINE | 0.000005 | 0.000005 |
| E | LYSINE HYDROCHLORIDE | 0.000005 | 0.000005 |
| E | VALINE | 0.000004 | 0.000004 |
| E | ARGININE | 0.000002 | 0.000002 |
| E | GLYCINE | 0.000002 | 0.000002 |
| E | ISOLEUCINE | 0.000002 | 0.000002 |
| E | LEUCINE | 0.000002 | 0.000002 |
| E | THREONINE | 0.000002 | 0.000002 |
| E | ZINC ACETATE | 0.000002 | 0.000002 |
| E | PROLINE | 0.000001 | 0.000001 |
| E | COPPER SULFATE | 0.00000033 | 0.00000033 |

Some mechanical properties, the homogeneity and the presence of bubbles into the compositions 1, 5 and 6 were determined and the corresponding results are summarized in Table 9 below.

TABLE 9

| Compositions | Polyacrylate crosspolymer-6 (% w/w) | Complex viscosity (Pa·s, 1 Hz) | $|\Delta|$ (top/bottom) of complex viscosity (Pa·s, 1 Hz) | Cross-over stress (Pa, 1 Hz) | Bubbles |
|---|---|---|---|---|---|
| 1 | 0.6 | 5.2 | 4.3 | 11.6 | No |
| 5 | 0.2 | 1.9 | 12.1 | 2.7 | No |
| 6 | 1 | 8.1 | 0.9 | 32.2 | Yes |

It comes out from these results that the composition with a lower concentration of polyacrylate crosspolymer-6 (that is to say 0.2% by weight, composition 5) discloses a high difference between complex viscosities (Pa·s, 1 Hz) of the top vs. the bottom of the pot, i.e. is heterogeneous (see composition 5 which has only 0.2% by weight of polyacrylate crosspolymer-6) whereas the compositions with a higher concentration of polyacrylate crosspolymer-6 (see compositions 1 in accordance with the invention and composition 6 which have respectively 0.6% by weight and 1.0% by weight of polyacrylate crosspolymer-6) are homogeneous such as it is desired.

However, among the compositions 1 and 6, only composition 1 in accordance with the invention discloses suitable appearance, texture and resistance to flowing.

Indeed, composition 6 displays visible bubbles; further, its high cross-over stress translates its difficulties for flowing and its important cohesion, such characteristics making it a product which is not conform for the purpose of the present invention.

In conclusion, these results show that a specific amount of polyacrylate crosspolymer-6 relative to the total weight of the composition, higher than 0.2% and lower than 1% by weight, need to be used for obtaining a stable composition.

Example 6: Effect of Hydroxyethylcellulose in a Composition in Accordance with the Invention Composition 1 was compared with another composition (composition 7) which was prepared according to the same process of preparation as the one for the composition 1 in accordance with the invention, as explained in example 1.

The composition 7 does not comprise hydroxyethylcellulose and more particularly comprises the components as shown in Table 10 below.

The compositions 1 and 7 are in accordance with the invention.

TABLE 10

| Phases | Components - INCI names | Composition 7 % by weight |
|---|---|---|
| A | WATER | QSP |
| A | DISODIUM EDTA marketed under Dissolvine NA2 ® by AkzoNobel | 0.100000 |
| B | HYDROLYZED HYALURONIC ACID marketed under PRIMALHYAL ® 50 by Solliance | 1.000000 |
| B | POLYACRYLATE CROSSPOLYMER-6 marketed under the name of SEPIMAX ™ ZEN by SEPPIC Company | 0.600000 |
| C | PHOSPHATE BUFFER SALINE | 12.712442 |
| C | SODIUM HYALURONATE CROSSPOLYMER-2 | 0.287500 |
| D | GLYCERIN | 0.250000 |
| D | METHYLGLUCOSIDE PHOSPHATE | 0.025000 |
| D | COPPER LYSINATE/PROLINATE | 0.012500 |
| E | GLUTATHIONE | 0.000010 |
| E | PYRIDOXINE HCl | 0.000010 |
| E | THIOCTIC ACID | 0.000010 |
| E | ACETYL CYSTEINE | 0.000005 |
| E | LYSINE HYDROCHLORIDE | 0.000005 |
| E | VALINE | 0.000004 |
| E | ARGININE | 0.000002 |
| E | GLYCINE | 0.000002 |
| E | ISOLEUCINE | 0.000002 |
| E | LEUCINE | 0.000002 |
| E | THREONINE | 0.000002 |
| E | ZINC ACETATE | 0.000002 |
| E | PROLINE | 0.000001 |
| E | COPPER SULFATE | 0.00000033 |

It has to be noted that the texture of composition 7 is far much more fluid and more silky texture than composition 1.

Some mechanical properties of the compositions 1 and 7 were determined and the corresponding results are summarized in Table 11 below.

It has to be noted that the presence of hydroxyethylcellulose does not influence the homogeneity of a composition comprising a crosslinked hyaluronic acid and a polyacrylate crosspolymer-6 but only its mechanical properties and its texture.

Indeed, according to this results the addition of hydroxyethylcellulose increases the viscosity and the cross-over stress (in other words the cohesion) of the composition and improves its touching, its fluidity, without significantly modifying its homogeneity.

Advantageously, the hydroxyethylcellulose provides a silky touch to the composition according to the invention.

The invention claimed is:

1. A sterile and topical cosmetic composition comprising, in a physiologically acceptable medium, an efficient amount of crosslinked hyaluronic acid and an efficient amount of polyacrylate crosspolymer-6,
  wherein the crosslinked hyaluronic acid is present in an amount ranging from about 0.10% to about 0.60% by weight with respect to the total weight of the composition, wherein:
  the polyacrylate crosspolymer-6 is present in an amount higher than 0.2% and lower than 1% by weight relative to the total weight of said composition, and
  said composition being devoid of preservatives.

2. The composition according to claim 1, wherein the crosslinked hyaluronic acid is in gel form.

3. The composition according to claim 2, wherein the crosslinked hyaluronic acid gel is present in an amount ranging from about 5% to about 99.5% by weight with respect to the total weight of the composition.

4. The composition according to claim 2, wherein the crosslinked hyaluronic acid gel comprises from about 10 mg/g to about 35 mg/g of total hyaluronic acid with respect to the total weight of the crosslinked hyaluronic acid gel.

5. The composition according to claim 1, further comprising an efficient amount of hydroxyethylcellulose.

6. The composition according to claim 5, wherein the hydroxyethylcellulose is present in an amount ranging from about 0.1% to about 5% by weight relative to the total weight of said composition.

7. The composition according to claim 1, further comprising at least one un-crosslinked hyaluronic acid or a salt thereof.

8. The composition according to claim 1, said composition being in the form of an aqueous gel.

9. The composition according to claim 1, packaged in a single-dose sterile reservoir comprising a capsule or a vial.

10. A method of reducing the signs of skin aging and/or caring for the skin of a subject who has previously been subjected to one or more aesthetic and/or cosmetic intervention(s) selected from the group consisting of an injection of a dermal filler composition, injection of botulinum toxin, peeling, micro-needling, mesotherapy, lipo-filling, injection of platelet-rich human plasma, radiofrequency, dermabra-

TABLE 11

| Compositions | Hydroxyethylcellulose (% w/w) | \|Δ\| (top/bottom) of complex viscosity (Pa · s, 1 Hz) | Complex viscosity (Pa · s, 1 Hz) | Cross-over stress (Pa, 1 Hz) |
|---|---|---|---|---|
| 1 | 0.8 | 4.3 | 5.2 | 11.6 |
| 7 | 0 | 7.1 | 0.4 | 2.5 | sion and lasers use comprising applying the sterile and topical cosmetic composition as defined in claim 1 to the subject in need thereof.

11. A cosmetic process for caring for the skin comprising at least the step of applying topically, on one or more skin surface(s), an effective amount of the sterile and topical cosmetic composition as defined in claim 1, to a subject who has previously been subjected to one or more aesthetic and/or cosmetic intervention(s) selected from the group consisting of injection of a dermal filler composition, injection of botulinum toxin, peeling, micro-needling, mesotherapy, lipo-filling, injection of platelet-rich human plasma, radiofrequency, dermabrasion and lasers use.

12. The cosmetic process according to claim 11, wherein said sterile and topical cosmetic composition is applied within one hour following the end of the one or more previous aesthetic and/or cosmetic intervention(s) and until one month after the end of the one or more previous aesthetic and/or cosmetic intervention(s).

13. The cosmetic process according to claim 11, wherein said sterile and topical cosmetic composition is applied once after the one or more previous aesthetic and/or cosmetic intervention(s).

14. The cosmetic process according to claim 11, wherein said sterile and topical cosmetic composition is applied on the one or more skin surface(s).

\* \* \* \* \*